US007325256B1

(12) United States Patent
Pecinka, Sr.

(10) Patent No.: US 7,325,256 B1
(45) Date of Patent: Feb. 5, 2008

(54) MALE/FEMALE URINARY AIDS

(76) Inventor: Edward L. Pecinka, Sr., 181 Sycamore Ave., Bethpage, NY (US) 11714

( * ) Notice: Subject to any disclaimer, the term of this patent is extended or adjusted under 35 U.S.C. 154(b) by 57 days.

(21) Appl. No.: 11/420,289

(22) Filed: May 25, 2006

(51) Int. Cl.
    *A47K 11/00* (2006.01)
(52) U.S. Cl. .......................... 4/144.1; 4/144.3; 4/144.4
(58) Field of Classification Search ...... 4/144.1–144.4; 141/331, 337; 604/347, 349
    See application file for complete search history.

(56) References Cited

U.S. PATENT DOCUMENTS

| 4,309,779 A | 1/1982 | Knight |
| 4,531,245 A | 7/1985 | Lowd et al. |
| 4,937,890 A * | 7/1990 | Tafur ............................ 4/144.4 |
| 5,091,998 A * | 3/1992 | Witzke ......................... 4/144.4 |
| 6,202,225 B1 | 3/2001 | Beck et al. |
| 6,668,388 B2 * | 12/2003 | Buttigieg ..................... 4/144.2 |

* cited by examiner

*Primary Examiner*—Tuan Nguyen

(57) ABSTRACT

The male/female urinary aids include devices for both male and female. The devices are light weight and highly portable. The inclusion of both male and female devices in the present aids enables a single person to transport both needed devices, as a wife might in her purse for both members of a couple. The devices are preferably made of plastic or the like and are easily cleansed. The fit of the three pieces of the female device provides easy cleaning. The capability of quick disassembly and collapsibility of the two-piece male device offers easy cleaning and compact storage. Both devices can be subjected to a washing machine or automatic dishwasher.

12 Claims, 3 Drawing Sheets

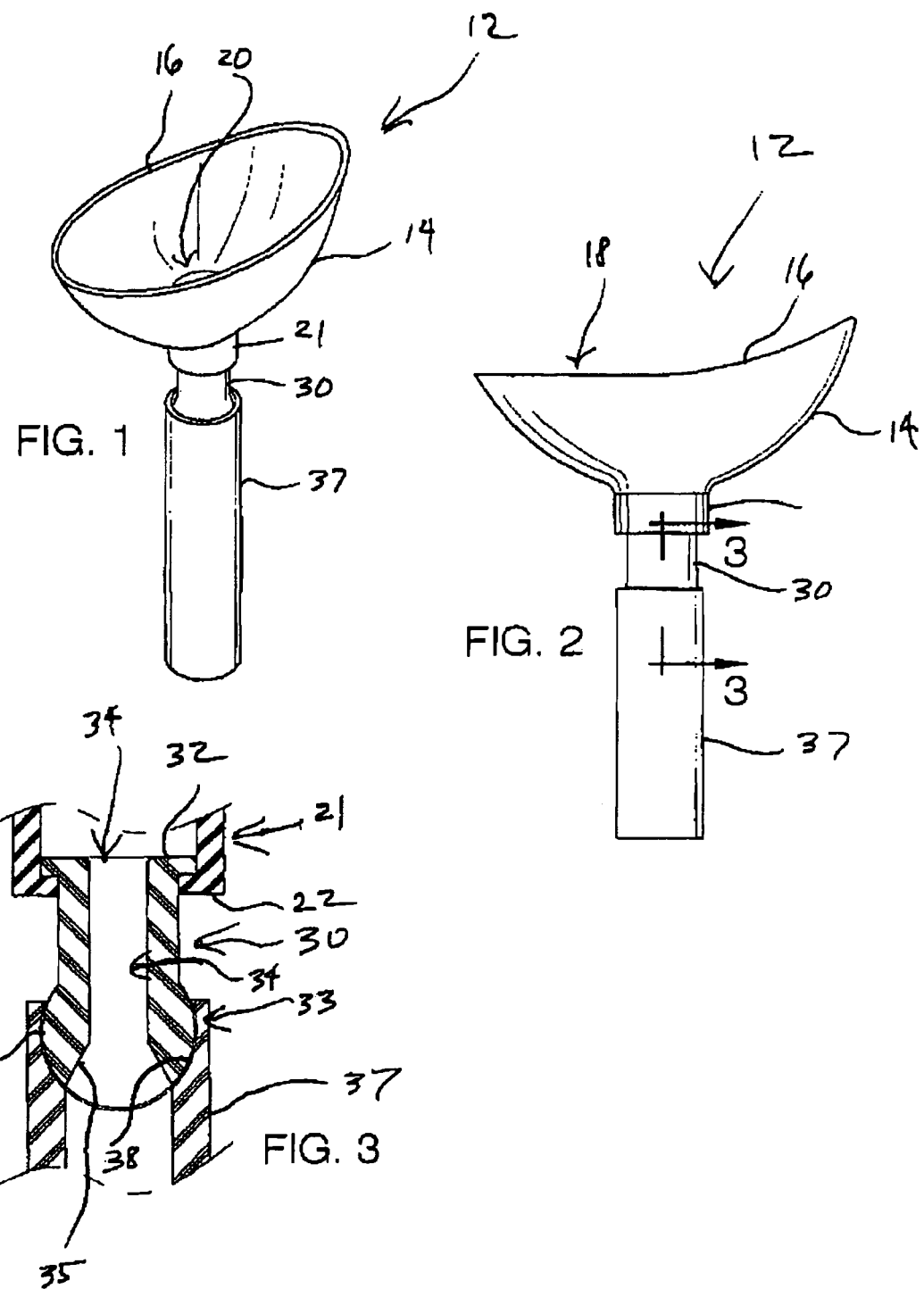

MALE/FEMALE URINARY AIDS

BACKGROUND OF THE INVENTION

The need for urinary aids which help to gather and control the flow of urine is established. The separate needs for control in voiding for both sexes are equally established. Sanitary conditions are a concern not only with home toilets but especially with public facilities. The present aids enable a female to avoid toilet contact and to control direction and splatter of urine. The aids also enable a male to control direction and splatter. Portability is an equally desirable feature, as is repeated use of the urinary aid. Universal fit, portability, light weight, reusability, practicality, and sexual differentiation are needs provided for by the present male/female urinary aids.

FIELD OF THE INVENTION

The male/female urinary aids relate to devices for aiding in collecting and directing urine and more especially to a male/female urinary aids which separately and portably addresses the needs of male and female.

DESCRIPTION OF THE PRIOR ART

Prior related art U.S. Pat. No. 4,309,779 issued on Jan. 12, 1982 to Knight teaches a urine collection device which is usable by men and women and has genital engaging feature. The device cannot provide the differentiation between the needs of the two sexes as does the present invention. U.S. Pat. No. 6,202,225 issued on Mar. 20, 2001 to Beck teaches a urinary device which covers the genitals and directs urination into a toilet allowing women to urinate while standing. The device does not address the needs of men. U.S. Pat. No. 4,531,245 issued on Jul. 30, 1985 to Lowd et al teaches a device which does not sufficiently address the needs of a male. The complexity of the device exceeds that needed by a male and exceeds that of the female device of the present invention.

While the above-described devices fulfill their respective and particular objects and requirements, they do not describe male/female urinary aids that provide for the advantages of the present male/female urinary aids. In this respect, the urinary aids substantially depart from the conventional concepts and designs of the prior art. Therefore, a need exists for improved urinary aids.

SUMMARY OF THE INVENTION

The general purpose of the male/female urinary aids, described subsequently in greater detail, is to provide urinary aids which have many novel features that result in improved male/female urinary aids which are not anticipated, rendered obvious, suggested, or even implied by prior art, either alone or in combination thereof.

To attain this, the male/female urinary aids include devices for both male and female. The devices are light weight and highly portable. The inclusion of both male and female devices in the present aids enables a single person to transport both needed devices, as example, as a wife might carry both devices in her purse for both members of a couple. The devices are preferably made of plastic or the like and are easily cleansed. The fit of the three pieces of the female device provides easy cleaning. The capability of quick disassembly of the two-piece male device offers easy cleaning. Both devices can be subjected to a washing machine or automatic dishwasher.

The male device helps men to avoid spraying during urination, spraying onto a toilet seat or beyond the toilet or the like. The female device eliminates the need for a woman to contact a toilet. Both devices offer easy storage and transport.

Thus has been broadly outlined the more important features of the improved male/female urinary aids so that the detailed description thereof that follows may be better understood and in order that the present contribution to the art may be better appreciated.

An object of the male/female urinary aids is to provide a device to aid in the gathering and control of urinary flow for both males and females.

Another object of the male/female urinary aids is to be portable.

A further object of the male/female urinary aids is to be basic in design.

An added object of the male/female urinary aids is to be produced inexpensively.

And, an object of the male/female urinary aids is to provide for repeated use.

Yet another object of the male/female urinary aids is to provide a collapsible male device.

Also, an object of the male/female urinary aids is to provide a partially pivotal female device.

Further, an object of the male/female urinary aids is to provide both male and female device which do not leak in use.

These together with additional objects, features and advantages of the male/female urinary aids will be readily apparent to those of ordinary skill in the art upon reading the following detailed description of presently preferred, but nonetheless illustrative, embodiments of the improved urinary aids when taken in conjunction with the accompanying drawings.

In this respect, before explaining the current embodiments of the improved male/female urinary aids in detail, it is to be understood that the male/female urinary aids are not limited in application to the details of construction and arrangements of the components set forth in the following description or illustration. Those skilled in the art will appreciate that the concept of this disclosure may be readily utilized as a basis for the design of other structures, methods, and systems for carrying out the several purposes of the male/female urinary aids. It is therefore important that the claims be regarded as including such equivalent constructions insofar as they do not depart from the spirit and scope of the urinary aids. It is also to be understood that the phraseology and terminology employed herein are for purposes of description and should not be regarded as limiting.

BRIEF DESCRIPTION OF THE DRAWINGS

FIG. 1 is a perspective view of the female device.

FIG. 2 is a side elevation view of the female device.

FIG. 3 is a cross sectional view of FIG. 2, taken along the line 3-3.

DETAILED DESCRIPTION OF THE DRAWINGS

With reference now to the drawings, and in particular FIGS. 1 through 6 thereof, the principles and concepts of the urinary aids generally designated by the reference number 10 will be described.

Figure 5:
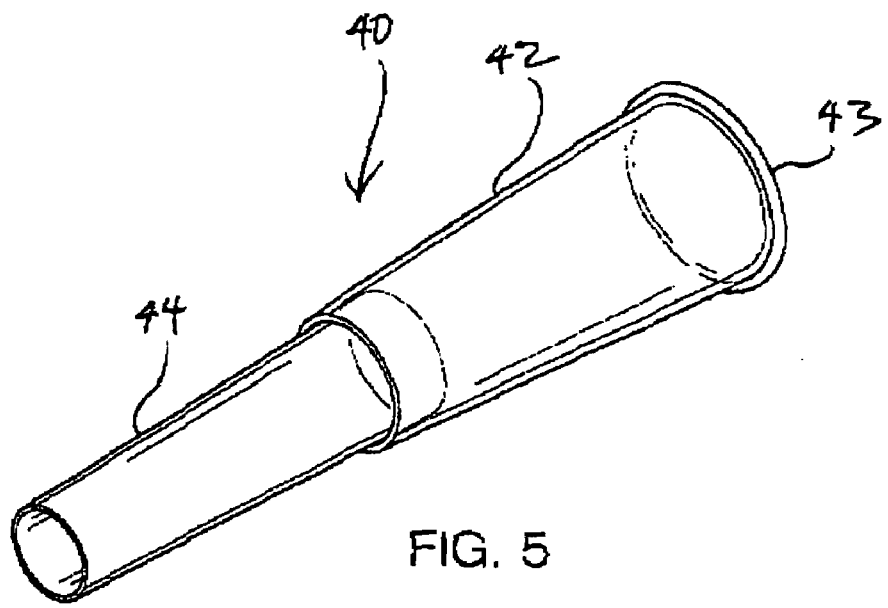
FIG. 5 is a perspective view of the male device, expanded.

Referring to FIGS. 1, 2, and 5, the urinary aids for male and female, referred to as aids 10, comprise, in combination, a three piece female collection aid device 12 and a collapsible two-piece male device 40. The female device 12 comprises a first piece forming a tapered elongated bowl 14. The rounded contoured lip 16 forms an upper edge of the upper larger opening 18 of the bowl 14. The lower smaller opening 20 of the bowl 14 opens into the hollow cylindrical neck 21. The neck 21 of the bowl 14 empties into the extension 30. The extension 30 empties into the transfer tube 37. The male device 40 comprises an upper open-ended hollow cone 42. The upper cone 42 has a large end and a small end, each end having a diameter. A rounded edge 43 is disposed on the large end of the upper cone 42. The lower cone 44 is slideably fitted within the upper cone 42. The lower cone 44 is temporarily wedged snugly within the upper cone 42 when slid downwardly and firmly. A leak proof seal is thereby temporarily obtained.

Referring to FIG. 3, the neck 21 extends from the lower opening 20 of the bowl 14 of the female device 12. An inward L-shaped angle 22 is disposed on a bottom of the neck 21. An opening is disposed through the neck 21 and the angle 22. A second piece of the female device 12 is formed as an extension 30. An outward inverted L 32 is disposed on a top of the extension 30. The L 32 is affixed to the angle 22 of the neck 21. The swivel ball 36 is disposed on a bottom of the extension 30. A passage 34 is disposed through the extension 30. A flare 35 is disposed within and at the bottom of the passage 34. The passage 34 enables smooth flow of urine into the transfer tube 37 and contributes to more controlled flow of urine out of the female device 12. The hollow transfer tube 37 is connected to the extension 30. The transfer tube 37 has a first end and a second end and a length therebetween. A female socket 38 is disposed on the first end of the transfer tube 37. The female socket 38 pivotally houses the swivel ball 36 of the extension 30. The swivel ball 36 and the female socket 38 comprise the swivel 33.

Figure 4:
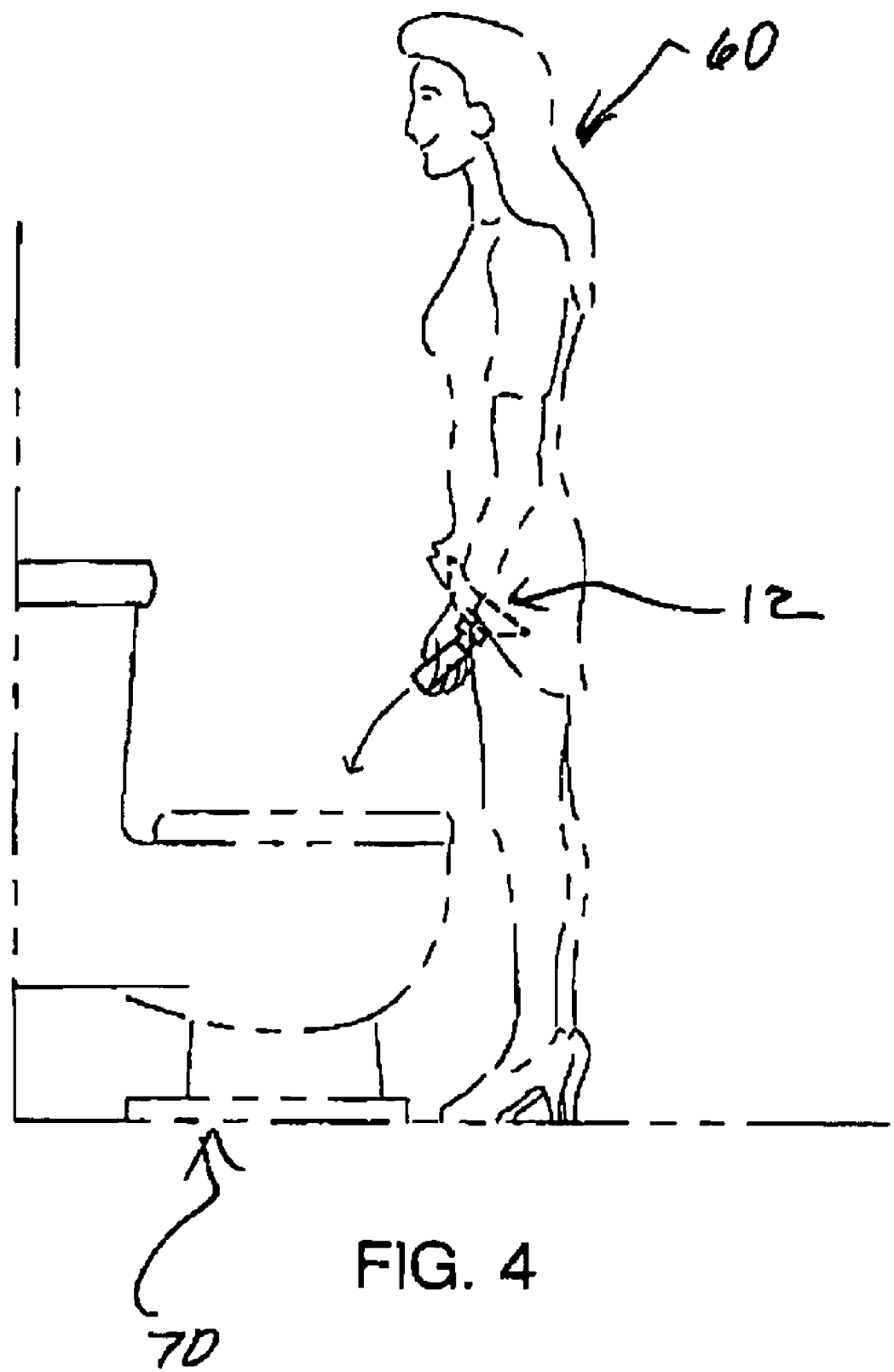
FIG. 4 is a side elevation view of a female using the female device.

Referring to FIG. 4, the upper opening 18 and lip 16 of the female device 12 are of a size to cover and extend beyond the genitalia of the female 60. The contoured lip 16 thereby provides a sealed contact with the flesh of the female 60, insuring against leakage from the flesh and female device 12. The contoured lip 16 insures comfortable fit. The flow characteristics of the female device 12 afford smooth, controlled flow into the toilet 70.

Figure 6:
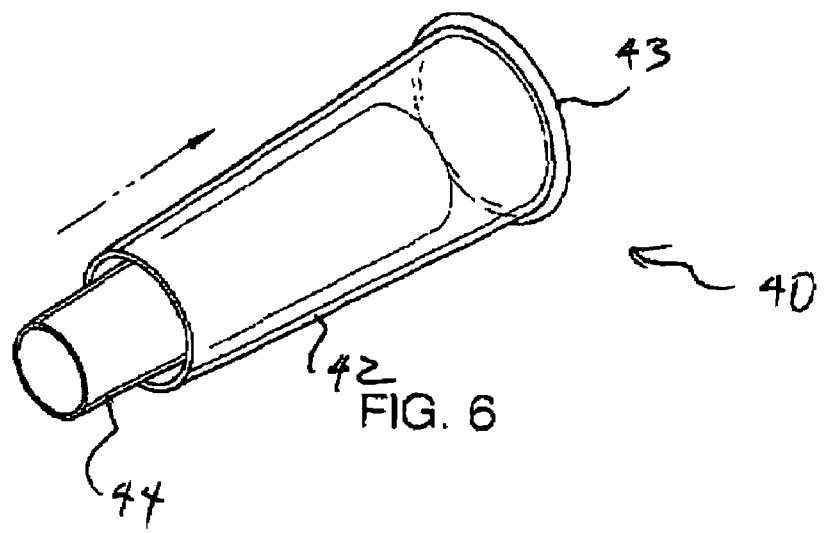
FIG. 6 is a perspective view of the male device, collapsed.

Referring to FIGS. 5 and 6, the collapsible two-piece male device 40 provides for selective collapsibility and disassembly for greater portability and storage. The ability to separate the upper cone 42 from the lower cone 44 of the male device 40 also aids in cleansing. The rounded edge 43 on the large end of the upper cone 42 of the male device 40 insures against delicate skin injury, as a penis fits inside the upper cone 42.

With respect to the above description then, it is to be realized that the optimum dimensional relationships for the parts of the urinary aids, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the urinary aids.

Directional terms such as "front", "back", "in", "out", "downward", "upper", "lower", and the like may have been used in the description. These terms are applicable to the embodiments shown and described in conjunction with the drawings. These terms are merely used for the purpose of description in connection with the drawings and do not necessarily apply to the position in which the urinary aids may be used.

Therefore, the foregoing is considered as illustrative only of the principles of the urinary aids. Further, since numerous modifications and changes will readily occur to those skilled in the art, it is not desired to limit the urinary aids to the exact construction and operation shown and described, and accordingly, all suitable modifications and equivalents may be resorted to, falling within the scope of the urinary aids.

What is claimed is:

1. Urinary aids for male and female, comprising, in combination:
   a female collection aid device, the female device comprising:
      a housing forming a tapered elongated bowl;
      an upper larger opening of the bowl, the upper opening of a size to cover and extend beyond the genitalia of the female;
      a lower smaller opening of the bowl;
      a neck from the lower opening of the bowl;
      an extension affixed to the neck;
      a swivel ball on a bottom of the extension;
      a passage through the extension and swivel ball;
      a hollow transfer tube having a first end and a second end, and a length therebetween;
      a female socket on the first end of the transfer tube, the female socket pivotally housing the swivel ball of the extension;
   a collapsible two-piece male device, the male device comprising:
      an open-ended hollow upper cone, the upper cone having a large end and a small end, each end having a diameter;
      an open-ended hollow lower cone, the lower cone having a large end and a small end, each end having a diameter, the lower cone for insertion within the upper cone, the large end diameter of the lower cone less than the large end diameter of the upper cone, the large end diameter of the lower cone greater than the small end diameter of the upper cone.

2. The urinary aids of claim 1 wherein the upper opening of the female aid comprises a rounded contoured lip, the lip providing for a sealed contact with the flesh of the female.

3. The urinary aids of claim 2 wherein the large end of the upper cone of the male device is comprised of a rounded edge.

4. The urinary aids of claim 3 wherein the swivel ball of the extension of the female device further comprises a flare at a bottom of the passage.

5. The urinary aids of claim 2 wherein the swivel ball of the extension of the female device further comprises a flare at a bottom of the passage.

6. The urinary aids of claim 1 wherein the large end of the upper cone of the male device is comprised of a rounded edge.

7. The urinary aids of claim 6 wherein the swivel ball of the extension of the female device further comprises a flare at a bottom of the passage.

8. The urinary aids of claim 1 wherein the swivel ball of the extension of the female device further comprises a flare at a bottom of the passage.

9. Urinary aids for male and female, comprising, in combination:
- a three piece female collection aid device, the female device comprising:
  - a housing first piece forming a tapered elongated bowl;
  - a upper larger opening of the bowl;
  - a lower smaller opening of the bowl;
  - a rounded contoured lip of the upper opening, the upper opening and lip of a size to cover and extend beyond the genitalia of the female, the lip thereby providing a sealed contact with the flesh of the female;
  - a neck from the lower opening of the bowl;
  - an inward L-shaped angle on a bottom of the neck;
  - an opening through the neck and the angle;
  - a second piece forming an extension of the female device;
  - an outward inverted L on a top of the extension, the L affixed to the angle of the neck;
  - a swivel ball on a bottom of the extension;
  - a passage through the extension;
  - a flare at a bottom of the passage;
  - a hollow transfer tube having a first end and a second end, and a length therebetween;
  - a female socket on the first end of the transfer tube, the female socket pivotally housing the swivel ball of the extension;
- a collapsible two-piece male device, the male device comprising:
  - an open-ended hollow upper cone, the upper cone having a large end and a small end, each end having a diameter;
  - a rounded edge of the large end of the upper cone;
  - an open-ended hollow lower cone, the lower cone having a large end and a small end, each end having a diameter, the lower cone for insertion within the upper cone;
  - the large end diameter of the lower cone less than the large end diameter of the upper cone, the large end diameter of the lower cone greater than the small end diameter of the upper cone.

10. The aids in claim 9 wherein a total length of the three-piece female device is about 3½ inches.

11. The aids in claim 10 wherein a total width of a widest part of the bowl of the female device is about 4 inches.

12. The aids in claim 9 wherein a total width of a widest part of the bowl of the female device is about 4 inches.

* * * * *